United States Patent [19]
Suzuki et al.

[11] Patent Number: 5,389,095
[45] Date of Patent: Feb. 14, 1995

[54] SUSPENDED ABSORBENT DIAPER ARTICLE

[75] Inventors: Migaku Suzuki, Kanagawa; Hiroaki Fukui, Saitama, both of Japan

[73] Assignee: Paragon Trade Brands, Inc., Federal Way, Wash.

[21] Appl. No.: 98,701

[22] Filed: Jul. 28, 1993

[51] Int. Cl.$^6$ .............................................. A61F 13/15
[52] U.S. Cl. .................................................. 604/385.2
[58] Field of Search ........................... 604/385.1, 385.2

[56] References Cited

U.S. PATENT DOCUMENTS

| | | | |
|---|---|---|---|
| 4,710,187 | 12/1987 | Boland et al. | 604/385.2 |
| 4,842,596 | 6/1989 | Kielpikowski et al. | 604/385.2 |
| 5,037,416 | 8/1991 | Allen et al. | 604/385.1 |

FOREIGN PATENT DOCUMENTS 0529641  3/1993  European Pat. Off. .

*Primary Examiner*—Jerome L. Kruter
*Attorney, Agent, or Firm*—Dressler, Goldsmith, Shore & Milnamow, Ltd.

[57] ABSTRACT

An absorbent article is disclosed comprising a liquid impermeable outer cover having a front section and a rear section, and an elongated absorbent element having a front end, a rear end and opposite side edges and including an absorbent material. The elongated absorbent element is supported at its front and rear ends on the outer cover in a suspended manner to extend longitudinally between the front and rear sections of the outer cover for spacing the opposite side edges from the outer cover. The elongated absorbent element further includes an elastic element so as to be elastically stretchable and contractable relative to the outer cover.

15 Claims, 2 Drawing Sheets

SUSPENDED ABSORBENT DIAPER ARTICLE

FIELD OF THE INVENTION

The present invention generally relates to absorbent articles such as infant or adult diapers, and more particularly to the absorbent article incorporating an absorbent member in a suspended manner therein.

BACKGROUND OF THE INVENTION

The disposable absorbent articles, such as infant or adult disposable diapers, are generally categorized into two types; a closed-type article such as a training pant, arid an open-type article having a flat configuration which includes front crotch and rear sections. Either of those absorbent articles typically comprises a liquid impermeable backsheet, a liquid permeable topsheet, and an absorbent core interposed therebetween, and are designed to effectively absorb and retain waste materials.

However, one drawback of such conventional integral absorbent articles is that they tend to be displaced away from a wearer's body by movement thereof. The displacement creates a space between the body and the absorbent article through which the waste materials leak. As a result, the desired absorbency of the absorbent core can not be fully utilized.

One attempt to overcome such drawback is illustrated in Japanese Kokai Patent No. Hei 3-202056. The Kokai patent proposes an absorbent article having a liquid impermeable stretchable topsheet with an aperture. A void space is provided between top and back sheets to improve conformability of the top sheet to the wearer's body and also to receive the waste materials therein which have passed through the aperture in the top sheet. This arrangement does not provide a better conformability of the absorbent core to the wearer's body since the topsheet is urged away from the absorbent core.

It is an object of the present invention to provide an absorbent article which is able to accommodate the body movement of a wearer for providing continuous conformity of an absorbent member to the wearer's body.

SUMMARY OF THE INVENTION

An absorbent article in accordance with the present invention comprises a liquid impermeable outer cover having a front section and a rear section, and an elongated element having a front end, a rear end and opposite side edges, and including an absorbent material. The elongated element is supported at the front and rear ends thereof on the outer cover in a suspended manner to extend longitudinally between the front and rear sections of the outer cover for spacing the opposite side edges from the outer cover. The elongated element further includes elastic material so as to be elastically stretchable and contractable relative to the outer cover.

In a particular embodiment of the present invention, the elongated element comprises a liquid permeable facing sheet, and a liquid impermeable elastic backing sheet intermittently secured to the facing sheet to form a plurality of channels therebetween. The absorbent material may be placed in selected ones of the channels.

In another aspect of the present invention, there is provided an absorbent article which comprises a liquid impermeable outer cover having a front section and a rear section, and an elongated absorbent member having a front end, a rear end and opposite side edges, and including an absorbent material. The absorbent article further comprises front and rear support members for respectively joining the respective front and rear ends of the absorbent member to the outer cover, so that the absorbent member extends longitudinally in a suspended manner between the front and rear sections of the outer cover for spacing the opposite side edges from the outer cover. One of the front and rear support members is elastically stretchable and contractable. Preferably, the front support member may be elastically stretchable and contractable.

In one embodiment of the present invention, both of the front and rear supports are elastically stretchable and contractable. In a particular embodiment, the elastically stretchable support member includes a plurality of parallel slits respectively extending longitudinally from a longitudinal end thereof to form a plurality of lips separated by the slits, and each of said lips is secured to the outer cover by a spot of securement.

Numerous other advantages and features of the present invention will become readily apparent from the following detailed description, the appended drawings, and the accompanying claims.

Detailed Description

Figure 1:
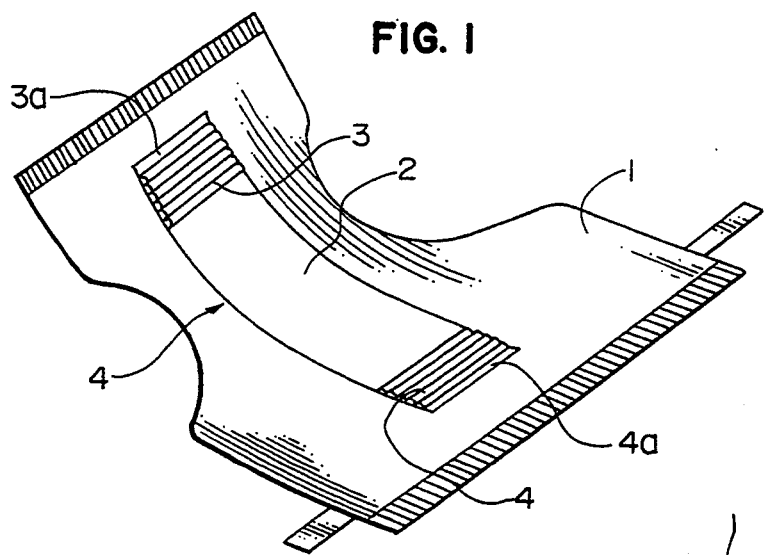
FIG. 1 is a perspective view of an absorbent article comprising a disposable diaper embodying the principles of the present invention.

While the present invention is susceptible of embodiments in various forms, there are shown in the drawings and will hereinafter be described various embodiments of the invention, with the understanding that the present disclosure is to be considered as an exemplification of the invention, and is not intended to limit the invention to the specific embodiments illustrated and described herein.

FIG. 1 is a perspective view of a disposable absorbent article comprising a disposable diaper in accordance with the present invention. The absorbent article comprises a liquid impermeable outer cover 1, an absorbent member 2 supported on the outer cover 1, and one or more elastic elements for connecting at least one of front and rear ends, preferably the front end, more preferably the both of front and rear ends of the absorbent member 2 to the outer cover 1 in a suspended manner. In the illustrated embodiment, the elastic element comprises a first elastic support 3 for connecting the front end of the absorbent member 2 to a front section of the outer cover 1, and a second elastic support 4 for connecting the rear end of the absorbent member 2 to a rear section of the outer cover 1. Although the outer cover 1 is illustrated as being an open-type having a flat configuration, it may be a closed-type having a pant-like configuration.

The absorbent member 2 may comprise absorbent material which has been conventionally incorporated in disposable diapers or sanitary napkins. Alternatively, the absorbent member 2 may comprise a facing sheet, a backing sheet and absorbent material interposed between the facing and backing sheets. The absorbent member 2 may further have a side barrier structure so as to be self-functional as an absorbent product. The generally rectangular, first elastic support 3 is at its one end connected to the front end of the absorbent member 2 by suitable connecting means, such as heat-sealing. The other end of the first elastic support 3 is connected to the outer cover 1 at a selected, rectangular region of securement 3a thereon. Likewise, the second elastic support 4 is at its one end connected to the rear end of the absorbent member 2, and is at its other end connected to the outer cover 1 at a selected, rectangular region of securement 4a on the outer cover 1.

Figure 2:
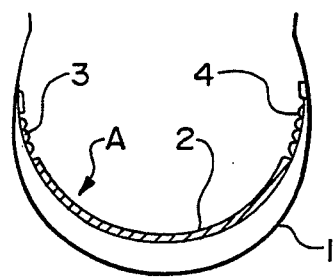
FIG. 2 is a longitudinal cross-sectional view of the absorbent article of FIG. 1.

The absorbent member 2 is of rectangular shape, having substantially the same width as the respective first and second elastic supports 3, 4 to together define an elongated strip-like element A. The elongated strip-like element A is suspended and extends longitudinally between front and rear sections of the outer cover 1. As illustrated in FIG. 2, the strip-like element A has a length such that an intermediate length portion thereof is positioned in a spaced relationship with the outer cover 1. More specifically, the strip-like element A is supportedly positioned relative to the outer cover 1 in a hammock-like manner so that the absorbent member 2 does not contact the outer cover 1. Accordingly, when the absorbent article is actually applied to the wearer, the absorbent member 2 is urged toward a crotch area of the wearer's body for close contact therewith by elastically stretching and contracting actions of the respective first and second elastic supports 3,4.

The first and second elastic supports 3,4 respectively elastically stretch and contract responsive to any movement of the wearer's body during the application of the absorbent article thereto, so that an optimum position of the absorbent member 2 is maintained relative to the wearer's body. This ensures that the absorbent capacity of the absorbent member 2 can be fully utilized. In a specific absorbent article construction wherein the outer cover 1 comprises an elastic material, the absorbent article tends to readily deform as the wearer's body moves. Even in such a construction, the optimum position of the absorbent member 2 can be still maintained relative to the wearer's body in accordance with the present invention. This permits the outer cover 1 to comprise an elastic material for providing a better feeling during use.

Figure 3:
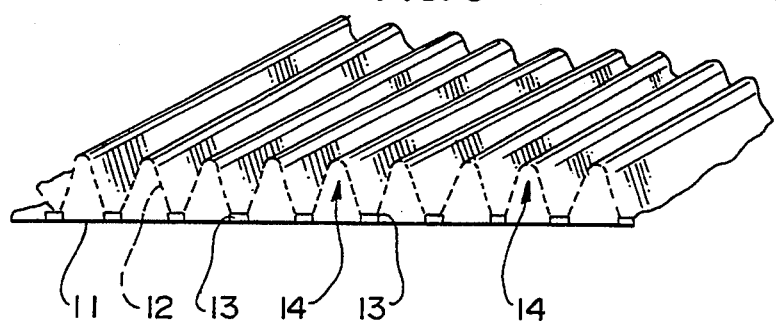
FIG. 3 is an enlarged, fragmentary perspective view of an elastic support.

The elastic supports 3, 4 of the present invention may comprise any suitable elastic material known in the art. Preferably, an elastic composite sheet as illustrated in FIG. 3 may be employed. The elastic composite sheet comprises an elastic material sheet 11, and a non-woven fabric 12 which is secured to at least one surface of the elastic material sheet 11 continuously in a first direction and intermittently in a second direction transverse to the first direction. The securement of these two elements is made along parallel securement lines 13 spaced from each other. The width of the non-woven fabric 12 is formed to be greater than that of the elastic sheet material 11 between adjacent securement lines 13, so that a plurality of parallel channels 14 are formed between the elastic material sheet 11 and the non-woven fabric 12. The elastic composite sheet is capable of stretching to the extent that the elastic material sheet 11 is extended to the same width as the non-woven fabric 12. A corrugated configuration of the soft non-woven fabric 12 further provides a comfortable feeling by softness to skin.

Suitable materials for the elastic material sheet 11 include a thin-layered sheet such as of natural or synthetic rubber, polyurethane film, polyurethane meltblown non-woven fabric, styrene-butadien block polymer film, or polyolefin elastomer film. When material cost, and adhesiveness to the non-woven fabric are taken into consideration, desirable materials include polyolefin elastomers such as EVA, LLDPE of ultra low density, ethylene propylene elastomer, ethylene-methylacrylate elastomer, or a blended combination of any of those polyolefin elastomers with synthetic rubber or styrene-ethylene-butadien•styrene block polymer (SEBS), or a co-extruded film of polyurethane elastomers and polyolefin elastomers.

Figure 4:
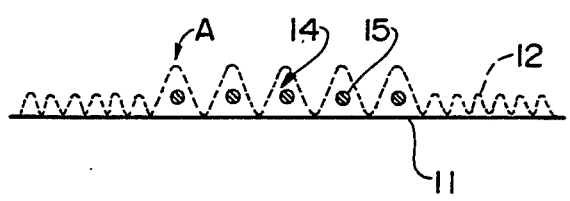
FIG. 4 is a diagrammatic, longitudinal cross-sectional view of an elongated member incorporating absorbent material and elastic supports.
Figure 5:
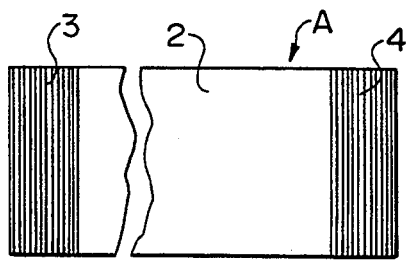
FIG. 5 is a diagrammatic plan view of an elongated member comprising an absorbent member and elastic supports.
Figure 6:
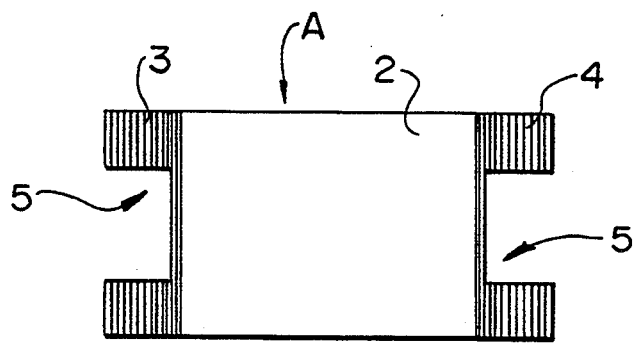
FIG. 6 is a diagrammatic plan view of an elongated member illustrating a central cutout in each of the elastic supports.

FIG. 4 illustrates one embodiment of the elongated, strip-like element A which integrally incorporates the absorbent member 2 and the first and second elastic supports 3, 4. The elongated member A comprises the elastic composite sheet, as shown in FIG. 3, with absorbent material 15 being placed in the channels 14 of the elastic composite sheet. In the illustrated particular embodiment, the channels 15 in a middle portion of the elastic composite sheet are configured to have a greater cross-sectional area than the remaining channels for enclosing the absorbent material 15 therein. The middle portion serves as the absorbent member 12, and end portions on opposite sides of the middle portions serve as the elastic supports 3, 4. The absorbent material may preferably comprise superabsorbent material, such as superabsorbent polymer which is capable of absorbing a large volume of liquids. The illustrated elastic composite sheet for the elastic supports 3, 4 has a relatively high stretchability in a direction transverse to the channel direction, and a relatively low stretchability in the channel direction which is limited to the stretching characteristics of the non-woven fabric 15. Accordingly, when the stretchability of the outer cover 1 is limited, the elastic composite sheet may have the same width as the absorbent member 2, and may be joined to the outer cover 1 over its full width as shown in FIG. 5. However, when the outer cover 1 is made from a highly stretchable material, a central cutout 5 (FIG. 6) may be preferably made in each of the first and second elastic supports 3, 4 to form a reduced area for securement to the outer cover 1, so that the stretchability of the outer cover 1 is less inhibited. In other words, the central cutouts 5 of the respective elastic supports 3, 4 serve to maintain the stretchability of the corresponding portions of the outer cover 1.

Figure 7:
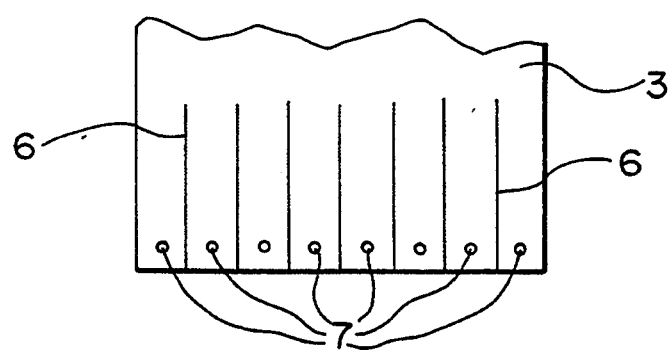
FIG. 7 is a fragmentary plan view of the elastic support illustrating a plurality of parallel slits formed therein.
Figure 8:
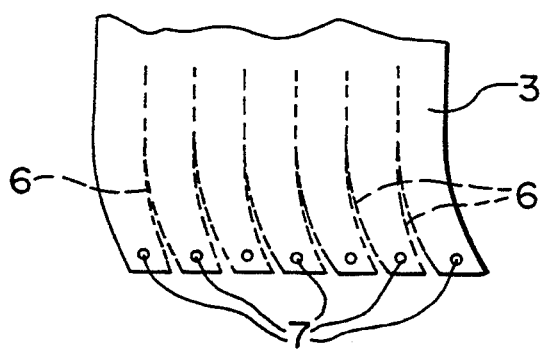
FIG. 8 is an explanatory view of the elastic support of FIG. 7 illustrating that the slits are caused to open up in responsive to the stretching of the outer cover.

Another embodiment for joining at least one of the elastic supports 3, 4 is illustrated in FIG. 7. A plurality of parallel slits 6 are formed at selected intervals to respectively extend from one end of the elastic support 3 in a direction transverse to the channel direction for defining a plurality of lips separated by the parallel slits 6. Each of the lips is secured to the outer cover 1 by a spot of securement 7. As the outer cover 1 is stretched, each of slits 6 is accordingly opened up as illustrated in FIG. 8, so that the outer cover 1 is able to stretch between the adjacent spots of securement 7. As such, the stretchability of the outer cover 1 is less inhibited.

From the foregoing, it will be observed that numerous modifications and variations can be effected without departing from the true spirit and the scope of the novel concept of the present invention. It is to be understood that no limitation with respect to the specific embodiments illustrated herein is intended or should be inferred. The disclosure is intended to cover by the appended claims all such modifications as fall within the scope of the claims.

What is claimed is:

1. An absorbent article comprising:
    a liquid impermeable outer cover having a front section and a rear section, and a central section between said front section and said rear section;
    an elongated absorbent element having a front end, a rear end and opposite side edges and including an absorbent material, said elongated element being supported at said front and rear ends thereof on said outer cover in a suspended manner to extend longitudinally between said front and rear sections of the outer cover for spacing a suspended portion of said elongated absorbent element, including said absorbent material between said front and rear ends thereof, from said central section of said outer cover, said elongated element further including elastic material so that said suspended portion of said elongated absorbent element is elastically stretchable and contractible relative to the outer cover so that said elongated absorbent element is urged toward a crotch area of a wearer of said article.

2. The absorbent article of claim 1, wherein said elastic material comprises a continuous elastic sheet supported between said front and rear sections of the outer cover.

3. The absorbent article of claim 2, wherein said elongated element further includes a liquid permeable facing sheet, said facing sheet being intermittently secured to said elastic sheet to form a plurality of channels therebetween, said absorbent material being placed in selected ones of said channels.

4. The absorbent article of claim 3, wherein said facing sheet is secured to said elastic sheet through longitudinally spaced, parallel lines of securement for forming the plurality of laterally-extending, parallel channels.

5. The absorbent article of claim 4, wherein said absorbent material is placed in the channels in a middle portion of the elongated element.

6. The absorbent article of claim 3, wherein said selected ones of the channels have a cross-sectional area greater than that of the remaining channels.

7. The absorbent article of claim 1, wherein one of said front and rear ends of the elongated element is secured to said outer cover by a continuous lateral line of securement.

8. The absorbent article of claim 1, wherein one of said front and rear ends of the elongated element is secured to said outer cover by intermittent lateral line of securement.

9. The absorbent article of claim 1, wherein said outer cover comprises an elastically stretchable material.

10. The absorbent article of claim 1, wherein said absorbent material comprises superabsorbent material.

11. An absorbent article comprising:
    a liquid impermeable outer cover having a front section and a rear section, and a central section between said front section and said rear section;
    an elongated absorbent member having a front end, a rear end and opposite side edges and including an absorbent material;
    front and rear support members for respectively joining said respective front and rear ends of the absorbent member to said outer cover, so that the absorbent member extends longitudinally in a suspended manner between said front and rear sections of the outer cover for spacing a suspended portion of said elongated member, including said absorbent material, between said front and rear support members from said central section of said outer cover, at least one of said front and rear support members being elastically stretchable and contractible.

12. The absorbent article of claim 11, wherein said front support member is elastically stretchable and contractable.

13. The absorbent article of claim 11, wherein said front and rear support members are both elastically stretchable and contractable.

14. The absorbent article of claim 11, wherein one of said front and rear support members is liquid impermeable.

15. The absorbent article of claim 11, wherein said elastically stretchable support member includes a plurality of parallel slits respectively extending longitudinally from a longitudinal end thereof to form a plurality of lips separated thereby, each of said lips being secured to the outer cover by a spot of securement.

* * * * *